United States Patent
Yoon (10) Patent No.: US 6,419,626 B1
(45) Date of Patent: Jul. 16, 2002

(54) SURGICAL INSTRUMENT ENDOSCOPE WITH CMOS IMAGE SENSOR AND PHYSICAL PARAMETER SENSOR

(76) Inventor: InBae Yoon, 11886 Farside Rd., Ellicott City, MD (US) 21042

( * ) Notice: Subject to any disclaimer, the term of this patent is extended or adjusted under 35 U.S.C. 154(b) by 0 days.

(21) Appl. No.: 09/334,635

(22) Filed: Jun. 17, 1999

Related U.S. Application Data (60) Provisional application No. 60/096,234, filed on Aug. 12, 1998.

(51) Int. Cl.$^7$ ................................................ A61B 1/05
(52) U.S. Cl. ..................... 600/109; 600/103; 600/117; 600/104
(58) Field of Search ................................ 600/102, 103, 600/112, 109, 117, 118, 474, 104

(56) References Cited

U.S. PATENT DOCUMENTS

| | | | |
|---|---|---|---|
| 4,878,485 A | | 11/1989 | Adair |
| 5,217,003 A | | 6/1993 | Wilk |
| 5,383,880 A | | 1/1995 | Hooven |
| 5,396,880 A | | 3/1995 | Kagan et al. |
| 5,398,685 A | * | 3/1995 | Wilk et al. .................. 600/437 |
| 5,402,769 A | * | 4/1995 | Tsuji .......................... 600/109 |
| 5,406,938 A | | 4/1995 | Mersch et al. |
| 5,408,998 A | | 4/1995 | Mersch |
| 5,417,210 A | | 5/1995 | Funda et al. |
| 5,467,762 A | * | 11/1995 | Sauer et al. ................. 600/114 |
| 5,536,234 A | | 7/1996 | Newman |
| 5,547,455 A | * | 8/1996 | McKenna et al. ........... 600/113 |
| 5,569,183 A | | 10/1996 | Kieturakis |
| 5,573,493 A | | 11/1996 | Sauer et al. |
| 5,734,418 A | * | 3/1998 | Danna .......................... 348/76 |
| 5,817,015 A | | 10/1998 | Adair |
| 5,840,013 A | | 11/1998 | Lee et al. |
| 5,893,712 A | | 4/1999 | Stone et al. |
| 5,919,130 A | | 7/1999 | Monroe et al. |
| 6,086,528 A | * | 7/2000 | Adair .......................... 600/110 |

* cited by examiner

*Primary Examiner*—John P. Leubecker
(74) *Attorney, Agent, or Firm*—Blank Rome Comisky & McCauley LLP (57) ABSTRACT

A surgical endoscopic instrument for visualizing anatomical tissue and including a tubular barrel carrying an endoscope with a CMOS image sensor and a physical parameter (e.g., temperature) sensor carried on the shaft. CMOS image sensors are fabricated on a single substrate or chip, with all of the required image signal processing circuitry, using the economical CMOS process. The CMOS image sensor is preferably mounted onto the distal end of the endoscope shaft and may include a light source for illuminating the field of visualization. In an alternative embodiment, the endoscope has a fixed objective lens carried on the distal end of a tubular body and a lens train or fiber optic bundle transmits the endoscopic image proximally to a CMOS sensor located in the hand piece. In the present invention, a single semiconductor substrate or chip has a CMOS imaging sensor with, preferably, a microprocessor and the associated signal processing circuitry for generating image signals for transmission to a display and to a data logging computer, outside the body. The surgical instrument carrying the CMOS image sensor preferably includes a distally mounted display, preferably a Liquid Crystal Display (LCD), mounted on a flexible stalk for convenient repositioning during a surgical procedure.

24 Claims, 6 Drawing Sheets

SURGICAL INSTRUMENT ENDOSCOPE WITH CMOS IMAGE SENSOR AND PHYSICAL PARAMETER SENSOR

This application claims the benefit of U.S. provisional application No. 60/096,234, filed Aug. 12, 1998.

RELATED APPLICATION DATA

This application is related to applicant's copending applications 08/847,187 and 08/847,254 (both filed May 1, 1997), as well as 08/366,285 (filed Dec. 29, 1994), 08/377,723 (filed Jan. 25, 1995), 08/401,002 (filed Mar. 9,1995), 08/585,875 (filed Jan. 16, 1996), 08/758,648 (filed Nov. 27, 1996), 60/085,242 (filed May 13, 1998), 60/085,243 (filed May 13, 1998), 60/089,660 (filed Jun. 17, 1998), and 60/093,069 (filed Jul. 16, 1998), the entire disclosures of which are incorporated herein by reference.

BACKGROUND OF THE INVENTION

1. Field of the Invention

The present invention pertains to an apparatus and method for endoscopic and open surgery and, more particularly, to a surgical device carrying an endoscopic instrument with a solid-state image sensor and physical parameter sensor for sensing a physical parameter such as temperature.

2. Discussion of the Prior Art

Various procedures are accomplished in both open surgery and endoscopic surgery, and generally include multiple steps requiring various operating instruments. Open surgery refers to surgery wherein the surgeon gains access to the surgical site by a relatively large incision and endoscopic surgery refers to minimally invasive surgery wherein the surgeon gains access to the surgical site via one or more portals through which an endoscope is introduced to view the surgical site and through which instruments having end effectors, such as forceps, cutters, needle holders, cauterizers, and the like, are introduced to the surgical site.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn, leaving the sleeve in place to form a portal in the cavity wall for the introduction of instruments such an endoscopes, scissors, forceps, needle holders and the like, into the anatomical cavity. The various end effectors at the distal end of the instrument are manipulated by the surgeon using controls disposed at the proximal end of the instrument while viewing the end effectors using the endoscope.

Endoscopes have included a variety of transducers such as vidicons (i.e., closed circuit television camera tubes) and solid-state Charge Coupled Devices (CCDs) for converting image light into electrical image signals for transmission to a viewing screen in the operating room (OR). CCD solid-state image sensors provide the benefits of small size and flexibility in image sensor placement, but are relatively difficult and expensive to implement in medical instruments, since CCD sensor signals require processing through complex and expensive ancillary equipment, if a usable image is to be displayed.

There are a number of situations, particularly when performing endoscopic surgery, in which it is desirable to measure temperature, pressure, pH or other physical parameters, while visualizing an object in the body. A number of surgical instruments have included diverse sensors for taking physical parameter measurements. CCD image sensors are produced using a technology unlike that used in fabricating other, high volume solid-state devices such as analog and digital signal processing transistor circuits, and so any attempt to combine a CCD image sensor with another kind of physical parameter sensor necessarily requires a separately fabricated device for installation near the CCD device. See, for example, U.S. Pat. No. 5,508,740 (to Miyaguchi et al.) disclosing a CCD image sensor for use in an analytical instrument and packaged with a separately fabricated temperature sensing thermistor; this pieced-together structure is necessary because there is no practical CCD fabrication method for combining an image sensor and a physical parameter sensor onto a single chip or substrate.

Endoscopic instruments, in general, also have been so expensive to use, sterilize and maintain that only surgeons in well-funded medical facilities have had access to instruments providing visualization in the body. There has been a long-felt need to move the site of medical care out of the OR to the hospital bed side or to an out-patient care facility. Endoscopic visualization could become an important component of patient-side care, were it available at a manageable price, and could be used for monitoring, as opposed to diagnosis, since endoscopic visualization and physical parameter monitoring could be performed daily or weekly, at bed side. If an economical, disposable alternative were available, endoscopic instruments for use at the bed side, in out-patient care, in ambulances or in the home could be provided for use in wide variety of medical and dental applications.

OBJECTS AND SUMMARY OF THE INVENTION

Accordingly, it is an object of the present invention to provide an economically implemented solid-state color image sensor and physical parameter sensor for generating an image ready signal and a physical parameter signal in an endoscopic instrument adapted to view organ or tissue structures or foreign objects, in the body.

Another object is to integrate a solid-state image sensor with a second physical parameter sensor on a single semiconductor substrate.

It is also an object of the invention to provide an endoscopic device having a Complimentary Metal Oxide Semiconductor (CMOS) solid-state image sensor with a physical parameter sensor, such as a temperature sensor, integrally fabricated onto a single substrate.

Another object of the present invention is to fabricate an economical, disposable endoscope having a solid state color image sensor and inexpensively manufactured objective optical lenses, incorporated into an easily manipulated form, for use at patient side.

Yet another object of the present invention is integrating a disposable endoscope into a surgical instrument having an end effector (e.g., forceps) of a selected length, and optics adapted to provide a useable image for the selected end effector length, providing visibility in the body during surgical instrument use.

The aforesaid objects are achieved individually and in combination, and it is not intended that the present invention be construed as requiring two or more of the objects to be combined unless expressly required by the claims attached hereto.

The present invention is generally characterized in an instrument for visualizing anatomical tissue and organ structures or foreign objects, in the body, and usually including an elongate hollow tubular shaft and an endoscope having a housing carrying a proximal end. The tubular shaft distal end is adapted to be inserted through a portal and into the body and includes a complementary metal oxide semiconductor (CMOS) image sensor carried on the shaft. By portal, it is meant either incised or natural openings in the body.

The CMOS image sensor substrate may also include a second physical parameter. sensor such as a thermistor temperature sensor. A thermistor (i.e., thermal resistor) is a semiconductor-based temperature measurement device for measuring a change in resistivity in a semiconductor with changing temperature, in which resistance decreases with increasing temperature. MOS current mirror circuits are used to provide an output voltage varying with sensed temperature (see, e.g., U.S. Pat. No. 5,347,149, to Kimura, the entire disclosure of which is incorporated herein by reference). In the present invention, a single semiconductor substrate or chip has a CMOS imaging sensor and a temperature sensing thermistor fabricated thereon with, preferably, a microprocessor and the associated signal processing circuitry for generating image signals and temperature measurement signals for transmission to a display and/or a data logging computer, outside the body.

CMOS image sensor and physical parameter sensor are preferably simultaneously fabricated using the economical CMOS process, an Integrated Circuit (IC) fabrication technology combining enhancement mode N-channel (NMOS) and enhancement mode Pchannel (PMOS) Field Effect Transistors (FETs) on a single substrate to form logic gates, memory cells, or other devices. CMOS image sensors are readily fabricated using the CMOS process and incorporate, on a single substrate (or chip), image sensing pixels and the required image signal processing circuitry for converting periodically sampled pixel voltage levels into an image ready signal adapted for display on, preferably, a color image display.

Examples of CMOS image sensors, generally, include U.S. Pat. No. 5,225,696 (to Bahraman) disclosing an image sensor with MOS photodetectors; U.S. Pat. No. 5,461,425 (to Fowler et al.) discloses a CMOS image sensor with pixel level A/D conversion on a single chip 10; U.S. Pat. No. 5,614,744 (to Merrill) discloses a CMOS image sensor with active pixels incorporating anti-blooming isolation guard rings; U.S. Pat. No. 5,665,959 (to Fossurn et al.) discloses a CMOS image sensor with a focal-plane digital photon-counting array; and U.S. Pat. No. 5,708,263 (to Wong) discloses a CMOS image sensor photodetector array with a simplified pixel circuit allowing denser arrays of pixels to be fabricated onto a chip; the entire disclosures of each reference identified above are incorporated herein by reference.

The CMOS image sensor is integrated onto a substrate or chip, preferably incorporated into a sealed optics package including one or more objective lens elements (disposed along an optical axis) and a printed circuit board or substrate carrying electrical connections to the CMOS image sensor; the sealed optics package is mounted onto and carried by the distal end of the endoscope shaft. The endoscope may be aimed to provide the desired field of view of a surgical procedure or an object in the body and may include an: articulable ball joint having the CMOS imaging sensor and a light source for illuminating the field of visualization; the ball joint imaging sensor aim is preferably articulable or controllable from the instrument proximal end using control members (e.g., wires) connected to handle-mounted control wheels (as disclosed in FIG. 19 of Applicant's U.S. Pat. No. 5,437,680, the entire disclosure of which is incorporated herein by reference). In an alternative embodiment, the endoscope has a fixed objective lens carried on the distal end of a tubular body and a lens train or fiberoptic bundle transmits the endoscopic image proximally to a CMOS sensor located in a proximal housing or hand piece.

The CMOS pixel signal processing circuitry converts image light energy into image ready signal energy adapted for transmission out of the body through connecting wires or, optionally, over an RF, microwave, or acoustic data link to a receiver connected to an image display. The surgical instrument carrying the CMOS image sensor preferably includes a proximally mounted display, preferably a Liquid Crystal Display (LCD), mounted on a flexible stalk for convenient repositioning during a surgical procedure. The display is preferably releaseably connectable using a locking electrical connector, thereby permitting removal of the display before sterilizing or discarding the endoscopic instrument, after use.

The objective lens elements may be movable via a motorized focus control mechanism, as is known in the art, but are preferably fixed in position to give a depth of field providing an in focus image at all distances (from the barrel distal end) greater than a selected minimum in-focus distance. Fixed focus optics are more suitable to economical manufacture, as required in design of disposable optics.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 3a is a partial cross section of the surgical instrument distal end of FIG. 2 showing a cross section of the sealed optics package including the integral physical parameter measurement sensor, the cross section is taken in a plane parallel to the optical axis and perpendicular to the image plane.

FIG. 3b is an enlarged view of the sealed optics package including the integral physical parameter measurement sensor of FIG. 3a.

DESCRIPTION OF THE PREFERRED EMBODIMENT

Figures 1, 9:
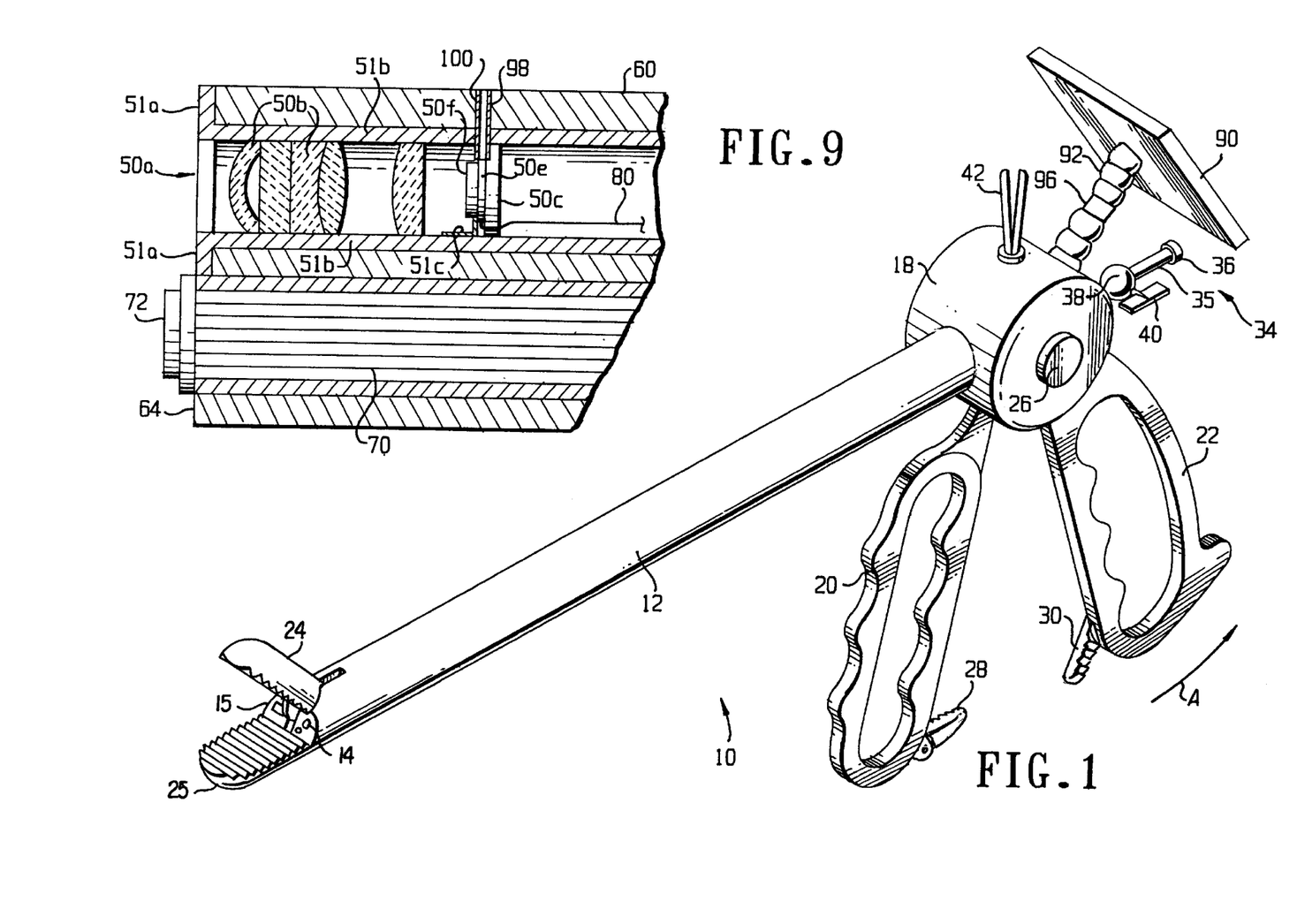
FIG. 1 is a perspective illustration of a surgical instrument including a solid-state endoscope having the integral physical parameter measurement sensor.
FIG. 9 is a partial cross-section of another embodiment of the endoscope distal end showing the integral physical parameter measurement sensor of a CMOS chip that communicates exteriorly of the endoscope.

In accordance with the present invention, as illustrated in FIG. 1, an endoscopic surgical instrument 10 can be used to visualize anatomical tissue, organ structures or foreign objects in an anatomical cavity or elsewhere in the body. While the instrument 10 is described hereinafter for use with a tubular portal sleeve (not shown) in endoscopic procedures, such as laparoscopy, the instrument can be used in open surgery or with catheters or other small and large diameter tubular or hollow cylindrical members providing access to small cavities (e.g., veins or arteries) or large cavities (e.g.,the abdomen); portal, for purposes of the present invention, is defined as any opening into the body, incised or natural.

Figure 2:
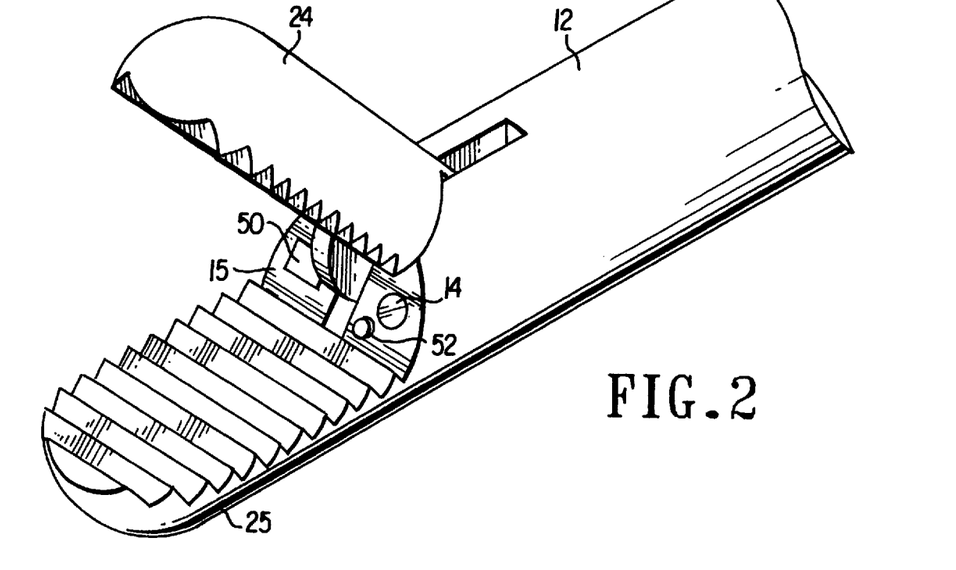
FIG. 2 is an enlarged perspective illustration of the distal end of the surgical instrument of FIG. 1.

The endoscopic instrument according to a first embodiment of the present invention is illustrated in FIGS. 1 and 2 and includes an elongate cylindrical barrel, or outer shaft 12 with a longitudinal axis and preferably having one or more elongated lumens or passages defined therein (preferably in the form of one or more channels, e.g., 14), a barrel distal end 15 for being disposed in the body and a barrel proximal end terminating in and carried by a housing 18 including an exterior wall enclosing an interior volume. Housing 18 includes scissor type handles 20 and 22 for controlling surgical instruments such as forceps having jaw members 24, 25 (as best seen in FIG. 2), or other end effectors. Housing 18 also includes a transversely located button 26 for selectively disengaging the scissor type handles 20 and 22 and permitting rotation of the handles about the axis of rotation (as indicated by the arrow A in FIG. 1). Handles 20, 22 are connected through a linkage mechanism (as is well known in the art) to at least one jaw; in the example of FIG. 1, movable jaw 24 is responsive to the separation between handles 20, 22, such that spreading handles 20, 22 apart opens jaw 24, separating jaw 24 from fixed jaw 2.

Handle rotation allows the surgeon to orient handles 20 and 22 in a desired manner, before or during surgery. The handles 20 and 22 also include serrated lock protrusions 28 and 30 to interlock and allow the position of handles 20 and 22 to be maintained in a state corresponding to a desired position of the end effectors (e.g., forceps jaws 24, 25). Lock protrusions 28 and 30 can be pivoted to a position to prevent interlock, if desired. Handles 20 and 22 are configured to be grasped while the surgeon's fingers pass through the openings in the handles or while the surgeon's fingers are wrapped around the outer portions of the handles, to increase comfort and adaptability.

The channel 14 in hollow barrel 12 is a lumen or passage adapted to receive elongate surgical instruments including a tubular body or member with a proximal end and a distal end being insertable at the proximal end of the barrel channel (e.g., at proximal end 34); channel 14 extends through proximal tubular body 35, which carries a Luer lock 36 and a spherical reservoir 38 for receiving a stop-cock valve 40, thereby allowing channel 14 to be selectably opened or sealed at the instrument proximal end. Housing 18 includes a cautery electrode connection 42 for removable electrical connection to a source of electrical energy for cauterizing tissue by passing electrical current through the end effectors (e.g., forceps jaws 24, 25 as illustrated in FIG. 2).

Figures 3A, 3B:
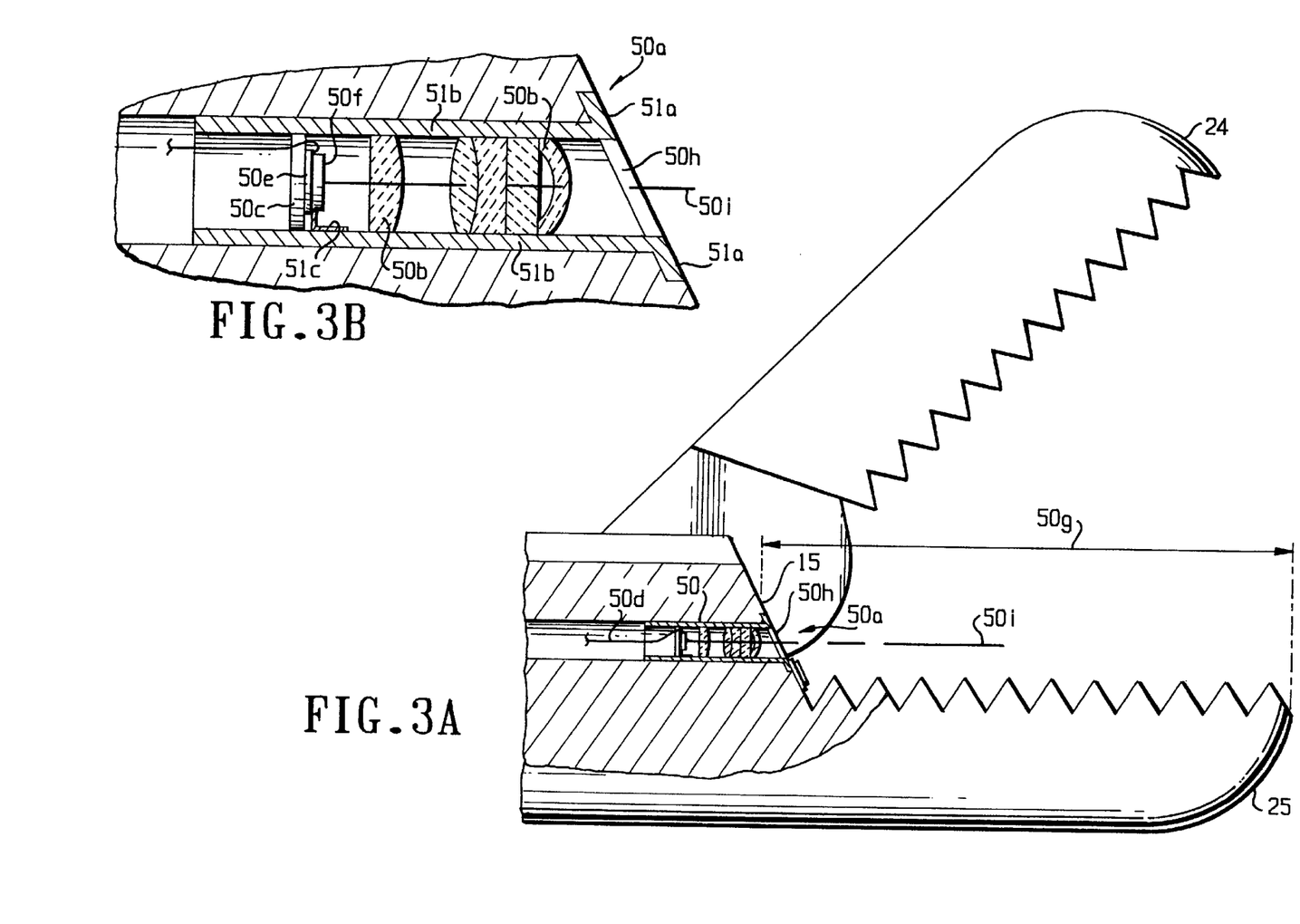

Turning now to FIGS. 2 and 3A and 3B, a substantially planar CMOS image sensor 50 includes a plurality of pixels (e.g., in a rectangular grid, 640 pixels by 480 pixels) and is affixed to and carried by instrument barrel distal end 15. The CMOS image sensor is integrated onto a chip 50e, preferably incorporated into a sealed optics package 50a including one or more objective lens elements 50b and a printed circuit board or substrate 50c carrying electrical connections between electrical conductors or wires 50d and the CMOS image sensor chip 50e; the sealed optics package 50a is mounted onto or integrated in the distal end 15 of the endoscope shaft 12, preferably proximate a fiber optic end 52.

By CMOS image sensor is meant a solid-state image sensor fabricated using the well known, economical, complementary metal oxide semiconductor (CMOS) process, i.e., the Integrated Circuit (IC) fabrication technology usually combining either or both of enhancement mode N-channel (NMOS) and enhancement mode P-channel (PMOS) Field Effect Transistors (FETs), preferably on a single substrate to form logic gates, memory cells, or image sensor pixels. CMOS image sensors are fabricated using the CMOS process and preferably incorporate, on a single substrate (or chip), image signal processing, memory, and data transmission circuitry to generate image ready signals and transfer the image ready signals out of the body. By image ready signal is meant a signal processed and adapted to be readily displayed on an image display. Any of several standards for image signal processing and transmission are suitable; for example, signal processing circuits on chip 50e can convert periodically sampled individual pixel voltage (or current) levels into a National Television System Committee (NTSC) image signal for transmission out of the body and display on an NTSC compatible image display (e.g., a television).

The CMOS image sensor 50 preferably has a plurality of MOS pixel circuits integrated onto chip 50e proximate a Red-Green-Blue (RGB) mosaic color filter panel 50f (as shown in FIG. 3) constituted by a mosaic arrangement of red, green, and blue color filters (or optionally, cyan, magenta and yellow color filters), thus permitting any single pixel to receive either red, green or blue (or cyan, magenta and yellow) filtered light energy. The color mosaic filter panel 50f is disposed on the optical axis of optics package 50a, ahead of the transverse imaging surface of the CMOS chip 50e. The pixels receiving red, green, and blue light generate, respectively, red, green, and blue pixel light intensity values, for color image ready signal generation. The lens elements 50b comprising the objective lens in sealed optics package 50a are preferably fixed in position providing a fixed depth of field at an image plane substantially coincident with a plane containing the pixels of CMOS image sensing chip 50e. The optical axis 50i (shown as a dotted line through sealed optics package 50a in FIG. 3) extends linearly from the image light transmissive, sealed protective cover or window 50h mounted on barrel distal end 15, proximally to image sensing chip 50e being disposed transverse thereto, in the image plane. The objective lens comprised of lens elements 50b focuses an image corresponding to the endoscope field of view at the image plane intersecting and transverse to the optical axis 50i. The objective lens is preferably fixed focus, meaning that a fixed depth of field is provided having a selected minimum in-focus distance 50g.

The objective lens elements 50*b* in sealed optics package 50*a* are selected and positioned to define a focal plane coincident with the image plane of image sensor chip 50*e*. Optionally, the objective lens elements 50*b* may be individually movable using a motorized focus control mechanism and may also provide variable magnification (i.e., zoom), as is known in the art. In the preferred embodiment, however, the lens elements are fixed in position to provide an in-focus image at all distances from the barrel distal end 15 greater than selected minimum in-focus distance 50*g*. Fixed focus optics are preferred for disposable embodiments. As shown in FIGS. 3*a* and 3*b*, the fixed focus optics of the sealed optics package 50*a* provide a minimum focus distance 50*g* (i.e., a minimum distance from the objective lens elements for which an observed object will remain in focus) less than or equal to the length of the forceps jaw 25 (or the length of any other surgical instrument end effector), thus ensuring that the surgeon can see a focused image of objects just within the grasp of the end effector, and beyond.

The substrate or chip 50*e* including the CMOS image sensor also includes a second physical parameter sensor such as a thermistor temperature sensor. A thermistor (i.e., thermal resistor) is a semiconductor-based temperature measurement device for measuring a change in resistivity in a semiconductor with changing temperature; resistance decreases with increasing temperature and MOS current mirror circuits are included to provide an output voltage varying with sensed temperature. The semiconductor substrate or chip thus has a CMOS imaging sensor and a temperature sensing thermistor fabricated thereon with, preferably, a microprocessor and the associated signal processing circuitry for generating image signals and temperature measurement signals for transmission to a display and to a data logging computer, outside the body. Thus, one aspect of the present invention is a solid-state CMOS image sensor (including a plurality of image sensing CMOS pixel circuits) fabricated onto a single substrate with a temperature sensor fabricated onto the same substrate (or chip). In the embodiment illustrated in FIGS. 3A and 3B, sealed optics package 50*a* includes a physical parameter sensor on chip 50*e* for measuring the physical parameter of temperature. A physical parameter sensing input structure adapted to transmit thermal energy to the temperature sensor on chip 50*e* includes a distally exposed thermally conductive flange 51*a* which is thermally connected to a thermally conductive sidewall 51*b* for transmitting thermal energy to a thermally conductive connecting member 51*c* attached to the temperature sensing thermistor on chip 50*e*. The CMOS thermistor circuit is connected to a temperature data transmission circuit generating a temperature signal; the temperature data transmission circuit is also integrated onto chip 50*e*; the temperature signal is preferably communicated over electrical connection 50*d*.

As shown in FIG. 1, surgical instrument 10 preferably includes a distally mounted adjustable image display 90 carried on housing 18. Display 90 can be a Liquid Crystal Display (LCD), a flat panel plasma display or a High Intensity Discharge (HID) display, mounted on a flexible stalk 92 for convenient repositioning during a surgical procedure. The display is preferably releaseably connectable using a locking electrical connector 96, thereby permitting removal of display 90 before sterilizing or discarding endoscopic instrument 10, after use.

A proximal light source is carried within the interior volume of housing 18 and is selectively energized to provide illumination transmitted distally through a fiber optic waveguide within barrel 12 and radiated distally from fiber optic distal end 52. Light radiating distally from fiber optic end 52 illuminates substantially all of the field of view of CMOS image sensor 50 and can be turned on or off by operation of a micro-switch (not shown) carried on housing 18. The light source is powered electrically through a housing cable proximally terminated in an electrical connector, or via a battery preferably carried within housing 18.

In an alternative embodiment of the present invention illustrated in FIGS. 4, 5, 6, 7 and 8, a surgical instrument 56 has a housing carrying an elongate hollow barrel including a lumen or channel 58 with an elongate tubular endoscope 60 extending through at least a portion of barrel channel 58. Elongate tubular endoscope 60 includes a cylindrical member, body or barrel 62 having distal end 64 adapted to be slidably received within instrument channel 58 and opposite a proximal endoscope housing 66 carried upon endoscope proximal end 68. A light source is contained within housing 66 and provides light transmitted distally through a fiber optic bundle 70 terminating distally in fiber optic end 72.

Figures 4, 5:
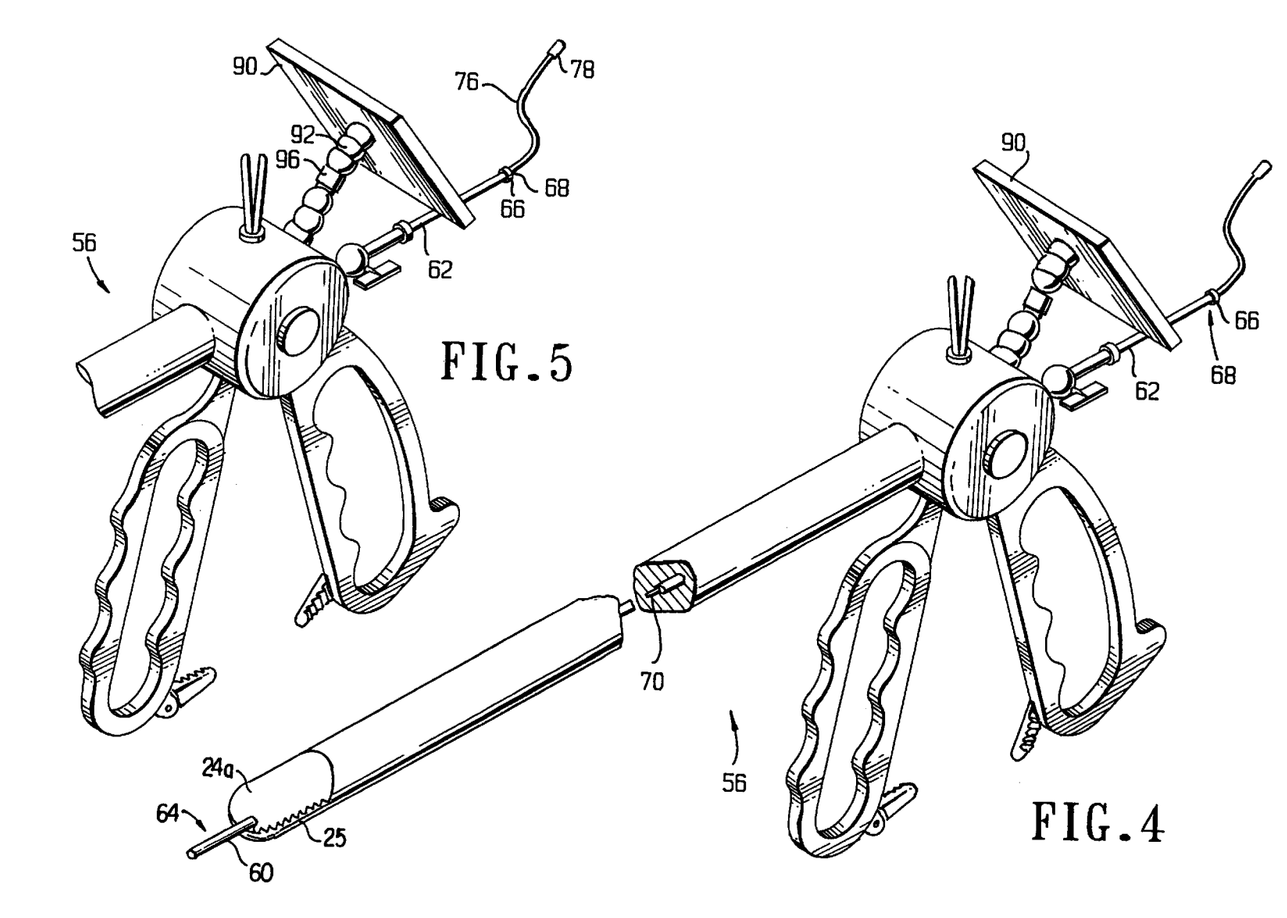
FIG. 4 is a perspective view of an alternative embodiment of the surgical instrument.
FIG. 5 is an enlarged perspective illustration of the proximal end of the surgical instrument of FIG. 4, with the detachable image display.
Figures 6, 7:
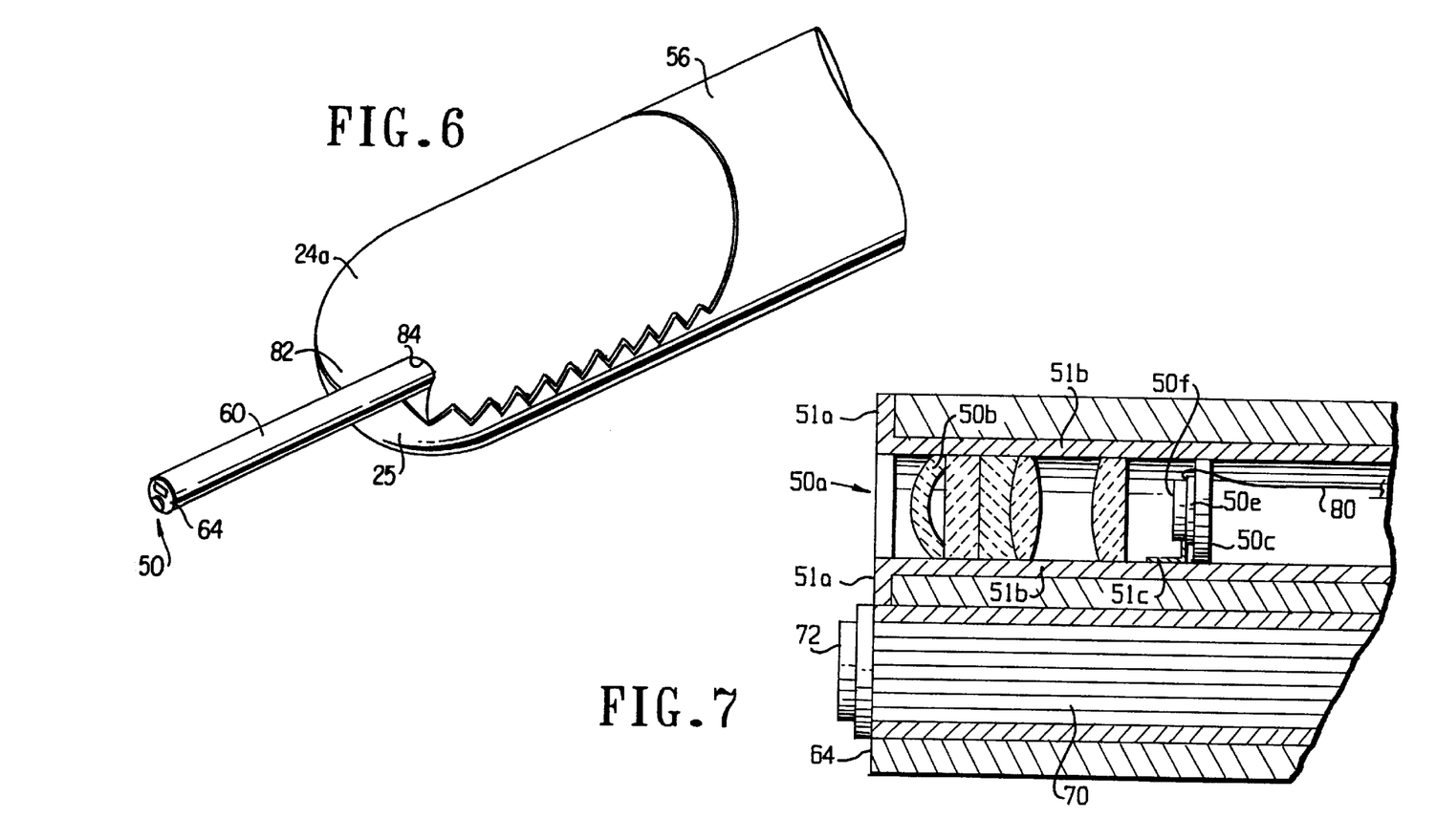
FIG. 6 is an enlarged perspective illustration of the distal end of the surgical instrument of FIG. 4.
FIG. 7 is a partial cross section of the endoscope distal end of FIGS. 4 and 6 showing a cross section of the sealed optics package including the integral physical parameter measurement sensor, the cross section is taken in a plane parallel to the optical axis and perpendicular to the image plane.

As shown in FIGS. 6 and 7, a CMOS image sensor 50 is affixed to and carried by distal end 64 of the elongate member or body 62 of tubular endoscope 60 and provides a distally aimed endoscope field of view. Light radiating distally from fiber optic end 72 illuminates substantially all of the field of view of CMOS image sensor 50 and is turned on or off by operation of a micro-switch (not shown) carried on housing 66. The light source is powered electrically through a housing cable 76 proximally terminated in an electrical connector 78 (as shown in FIG. 5).

CMOS image sensor 50 preferably includes a rectangular array (e.g., 640×480) of MOS pixel circuits integrated onto chip 50*e* proximate a Red-Green-Blue (RGB) mosaic color filter panel 50*f* (as shown in FIG. 7) constituted by a mosaic arrangement of red, green, and blue color filters (or, as above, cyan, magenta and yellow color filters), thus permitting any single pixel to receive either red, green or blue (or cyan, magenta and yellow ) filtered light energy. The color mosaic filter panel 50*f* is disposed on the optical axis of optics package 50*a*, ahead of the transverse imaging surface of the CMOS chip 50*e*. The pixels receiving red, green, and blue light generate, respectively, red, green, and blue pixel light intensity values, for color image signal generation. The lens elements 50*b* comprising the objective lens in sealed optics package 50*a* are preferably fixed in position providing a fixed depth of field at an image plane substantially coincident with a plane containing the pixels of CMOS image sensing chip 50*e*. The optical axis 50*i* (shown as a dotted line through sealed optics package 50*a* in FIG. 7) extends linearly from the image light transmissive, sealed protective cover or window 50*h* mounted on member distal end 64, proximally to image sensing chip 50*e* being disposed transverse thereto, in the image plane. The objective lens comprised of lens elements 50*b* focus an image corresponding to the endoscope field of view at the image plane intersecting and transverse to the optical axis 50*i*. The objective lens is fixed focus, meaning that a fixed depth of field is provided having a selected minimum in-focus distance (e.g., one centimeter).

Figure 8:
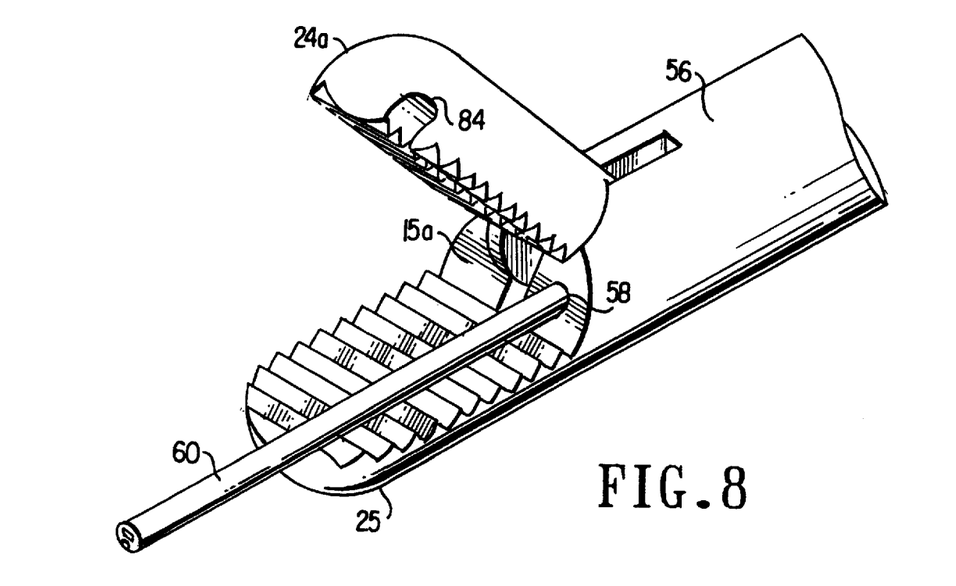
FIG. 8 is an enlarged perspective illustration of the distal end of the surgical instrument of FIG. 4, with the jaws shown in the open position.

The objective lens elements 50*b* in sealed optics package 50*a* are selected and positioned to provide a focal plane coincident with the image plane of image sensor chip 50*e*. Optionally, the objective lens elements 50*b* may be individually movable using a motorized focus control mechanism and may also provide variable magnification (i.e., zoom), as is known in the art. In the preferred embodiment, however, the lens elements are fixed in position to provide an in-focus image at all distances from the endoscope distal end 64 greater than the selected minimum in-focus distance. As shown in FIG. 7, the fixed focus optics of the sealed optics package 50*a* provide a minimum focus distance (i.e., a minimum distance from the objective lens window 50*h* or member distal end 64 for which an observed object will remain in focus) less than or equal to the length of fixed forceps jaw 25 (or the length of any other surgical instrument end effector), thus ensuring that the surgeon can see a focused image of objects just within the grasp of the end effector, and beyond, when the endoscope 60 is slidably positioned within channel 58 with endoscope distal end 64 aligned with (i.e., even with and not projecting beyond) barrel distal end 15*a*. Alternatively, endoscope 60 may be translated distally to project well beyond the barrel distal end 15*a* (as shown in FIG. 8) in which case objects beyond the minimum in focus distance (and further) will be in focus at the image plane coincident with CMOS image sensor chip 50*e*.

The semiconductor chip 50*e* includes a CMOS imaging sensor and, preferably, a microprocessor and a signal processing circuit for generating image-ready signals for transmission to a display and to a data logging computer, outside the body. Image signal data is transmitted proximally from CMOS image sensor 50, preferably via an image signal cable 80 running just within the exterior surface of barrel 62. Preferably, image-ready data is transmitted proximally and out of the body to a movably adjustable, releaseably connectable display 90 and/or to an image data logging recorder or computer (not shown) through an image data cable electrically connected with image signal cable 80.

In the embodiment of FIG. 7, the substrate or chip 50*e* including the CMOS image sensor also includes a second physical parameter sensor such as a thermistor temperature sensor and so the semiconductor substrate or chip thus has a CMOS imaging sensor and a temperature sensing thermistor fabricated thereon with, preferably, a microprocessor and the associated signal processing circuitry for generating image signals and temperature measurement signals for transmission to a display and to a data logging computer, outside the body. Thus, in the embodiment illustrated in FIG. 7, sealed optics package 50*a* includes a physical parameter sensor on chip 50*e* for measuring the physical parameter of temperature. A physical parameter sensing input structure adapted to transmit thermal energy to the temperature sensor on chip 50*e* includes a distally exposed thermally conductive flange 51*a* which is thermally connected to a thermally conductive sidewall 51*b* for transmitting thermal energy to a thermally conductive connecting member 51*c* attached to the temperature sensing thermistor on chip 50*e*. The CMOS thermistor circuit is connected to a temperature data transmission circuit generating a temperature signal; the temperature data transmission circuit is also integrated onto chip 50*e*; the temperature signal is preferably communicated over cable 80.

As noted above, in the embodiment of FIGS. 4, 5, 6, 7 and 8, endoscope 60 maybe advanced distally through channel 14, up to and beyond the distal end 82 of forceps jaws 24*a*, 25. Preferably at least one jaw 24*a* (or other end effector) includes a groove 84 to permit endoscope 60 (or another surgical instrument) to pass therethrough when the jaws are closed (as shown in FIG. 6).

As shown in FIGS. 4 and 5, surgical instrument 56 preferably includes proximally mounted adjustable image display 90 carried on a flexible stalk 92 for convenient repositioning during a surgical procedure and preferably releaseably connectable using a locking electrical connector 96, thereby permitting removal of display 90 before sterilizing or discarding endoscopic instrument 56 after use.

The endoscopic instruments of the present invention (e.g., 60) may be aimed to provide the desired field of view of a procedure and may include a sealed optics package in the form of an articulable ball joint having the CMOS imaging sensor and a light source for illuminating the field of visualization; the ball joint imaging sensor aim is preferably articulable or controllable from the instrument proximal end using wire control members connected to housing mounted control wheels.

In an alternative embodiment, the endoscope has a fixed objective lens carried on the distal end of a tubular body and a lens train or fiberoptic bundle transmits the endoscopic image proximally to a CMOS image sensor located in a housing (e.g., 18 or 66).

Another embodiment of the present invention is shown in FIG. 9. The embodiment in FIG. 9 is the same as shown in FIG. 7 except that a tube 98 extends from the chip 50*e* to the exterior of the tubular endoscope 60. The tube 98 defines a conduit 100 so that the chip 50*e* can be exposed to compressible or incompressible fluids that exist about the tubular endoscope 60. Preferably, the conduit 100 permits the physical parameters sensor to contact such fluids.

Figure 10:
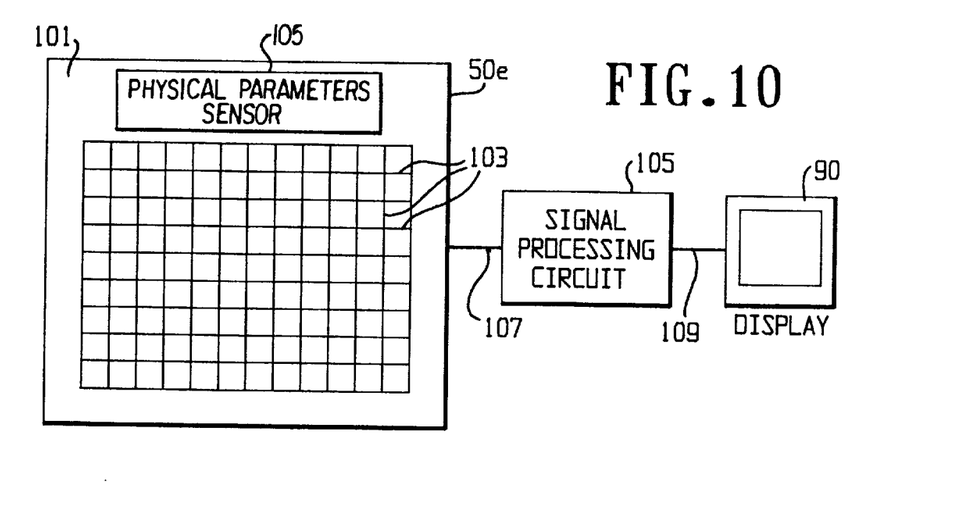
FIG. 10 is a diagrammatical view of the CMOS chip integrally formed with the physical parameters sensor in electrical connection with a signal processing circuit and a display.

In FIG. 10, the chip 50e is shown as an integrated sensor that includes a substrate of semiconductor material 101, a pixel array of light detecting elements 103 and a physical parameters sensor 105. The pixel array of light detecting elements 103 as well as the physical parameters sensor 105 are integrally formed with the substrate 101 to form an integrated sensor article. Preferably, the integrated sensor article is fabricated by a CMOS (complimentary metal oxide semiconductor) process which is known in the art. The chip 50e is electrically connected to a signal processing circuit 105 by an electrical connection 107. In turn, the signal processing circuit 105 is connected to the image display 90 by an electrical connection 109. Further, the signal processing circuit 105 is also integrally formed with the substrate 101 and connected to the pixel array of light detecting elements 103 and the physical parameters sensor 105.

Although the integrated sensor article is shown by way of example using an endoscope typically used for grasping tissue or foreign bodies at the site, one of ordinary skill in the art would appreciate that integrated sensor can be used with any type of endoscopic instrument that can be used for both viewing a site internally of a living body and measuring at least one physical parameter adjacent the site. Thus, the integrated sensor includes the objective lens, the substrate of semiconductor material, the pixel array of light-detecting elements and at least one physical parameter sensor. The objective lens is mounted on the endoscopic instrument along the optical axis for focusing on an image at the site. The pixel array of light-detecting elements are mounted onto the substrate and positioned along the optical axis to receive the focused image in a form of light energy. The pixel array of light-detecting elements are operative to convert the light energy of the focused image into a plurality of digital electrical signals through subsequent processing and display exteriorly of the living body. At least one physical parameter sensor is mounted onto the substrate and is operative to measure at least one physical parameter adjacent the site.

With the embodiment using the tube and conduit 98 and 100, respectively, in FIG. 9, the physical parameter sensor is capable of measuring fluid temperature, fluid pressure, oxygen content of the fluid, carbon dioxide content of the fluid, pH of the fluid, conductivity of the fluid, electrolyte concentration and/or presence, glucose concentration and/or presence and other types of physical characteristics of the fluid commonly known in the art.

It will be appreciated that the endoscope of the present invention, in each of the embodiments described herein, provides visualization or organ structures, tissue structures, prostheses and other foreign objects within the body, and all are adapted to be inserted through any portal into the body. Portal, as used herein, means any incised or natural opening providing access into the body. CMOS image sensor, as used herein includes all solid state integrated circuits fabricated by the well known CMOS process producing chips having a plurality of pixels for converting image light energy into electrical image signal energy. Preferably, the CMOS image sensor and physical parameter sensor of the present invention include, on a single chip or integrated circuit, an image processing circuit for converting periodically sampled pixel voltage (or current) levels into an image ready signal and a temperature data circuit generating a temperature signal, where the image ready signal and the temperature signal are both adapted for transmission out of the body (e.g., by electric signal conduction through wires or by transmission through an RF, microwave, ultrasonic, acoustic or fiber-optic data channel). An image ready signal, as used herein, means a signal processed and formatted (or otherwise adapted) for display on an image display or monitor. A CMOS image sensor pixel, as used herein, means a CMOS image sensor picture element, usually occupying a defined region in a two dimensional array, for gathering light in that region. For color images, a red pixel, a green pixel, and a blue pixel occupy three subregions within a color pixel region and red, green and blue color optical filters are incorporated into a color mosaic filter element and disposed adjacent to the respective CMOS image sensor pixel subregions. Depth of field, as used herein, describes the range of distances from the image sensor for which an object within the field of view will be in focus and resolved in sharp detail.

Figure 11:
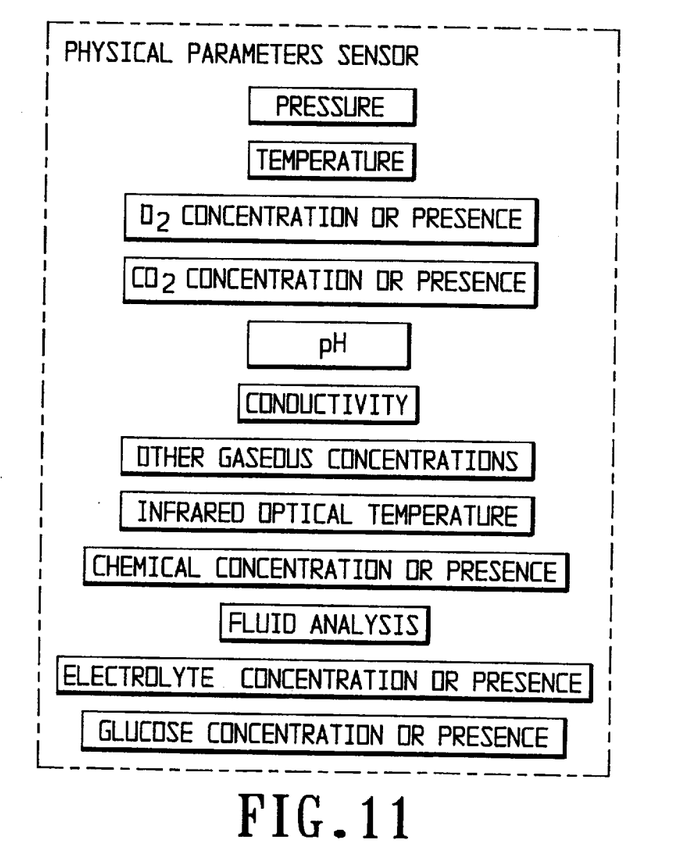
FIG. 11 is a diagrammatical view of the physical parameters sensor that includes any one or a combination of any ones of the listed physical parameters.

One of ordinary skill in the art would appreciate that the physical parameters sensor can be used to measure one or more physical parameters simultaneously. By way of example as shown in FIG. 11, the physical parameter sensor measures pressure, temperature, oxygen concentration or presence, carbon dioxide concentration or presence, chemical concentration or presence, pH conductivity and/or other gaseous concentrations. Also, the physical parameters sensor can also be used to measure temperature by infrared optical means and perhaps conduct fluid analysis. In the embodiments illustrated herein, the physical parameter measured is temperature. However, a number of other solid state sensors are readily adapted to use in an endoscope with a solid state CMOS image sensor. In particular, the present invention is readily adapted to include a solid state pressure sensor, an infrared optical temperature sensor, a solid state pH sensor (see, e.g., U.S. Pat. No. 5,685,319, to Marett, the entire disclosure of which is incorporated herein by reference), and a sensor to detect the presence and/or concentration of one or more chemicals in the body such as glucose, sodium, potassium, chloride, urea, hematocrit, hemoglobin, oxygen (see e.g., U.S. Pat. No. 5,126,937, to Yamaguchi et al, the entire disclosure of which is incorporated herein by reference), carbon dioxide and others. Alternatively, fluid analysis sensor circuits such as those disclosed in U.S. Pat. No. 5,096,669 (to Lauks et al, the entire disclosure of which is incorporated herein by reference) can be included on a substrate with the CMOS image sensor in the endoscope of the present invention.

In as much as the present invention is subject to various modifications and changes in detail, the above description of a preferred embodiment is intended to be exemplary only and not limiting. It is believed that other modifications, variations and changes will be suggested to those skilled in the art in view of the teachings set forth herein. It is therefore to be understood that all such variations, modifications and changes are believed to fall within the scope of the present invention as defined by the appended claims.

I claim:

1. An endoscope for providing visualization of organ or tissue structures or foreign object, in a body, comprising:
   an elongate member having a longitudinal axis, a proximal end for being disposed externally and a distal end for being disposed in the body, said elongate member being adapted to be inserted through a portal into the body;
   a substantially planar complementary metal oxide semiconductor (CMOS) chip including an image sensor including a plurality of pixels and a pixel signal processing circuit generating a color image ready signal, converting image light energy into electrical color image ready signal energy, for transmission out of the body, said color image ready signal adapted to be viewed on a color image display;
   a repositionable mount carrying said image display and comprising a flexible stalk supporting an image display panel;
   said chip further including a physical parameter sensor;
   said CMOS image sensor being carried on said elongate member, adjacent said elongate member distal end;
   an objective lens carried on said elongate member distal end on an optical axis and focusing an image corresponding to an endoscope field of view at an image plane intersecting said optical axis; said CMOS image sensor being mounted with said CMOS image sensor pixels disposed substantially in said image plane and on said optical axis.

2. The endoscope of claim 1, said physical parameter sensor comprising a temperature sensor.

3. The endoscope of claim 1, further including at least one fixed focus objective lens element having a depth of field with a selected minimum in-focus distance for an in-focus image at the image plane.

4. The endoscope of claim 3, further comprising surgical instrument end effectors having a selected length substantially equal to or greater than said minimum in-focus distance.

5. The endoscope of claim 3, further including a color mosaic optical filter disposed between said CMOS image sensor and said objective lens, said color mosaic optical filter being disposed on said optical axis.

6. A surgical endoscopic instrument for viewing anatomical tissue or organ structures or other object in a body, comprising:
   a) an elongate hollow barrel having a longitudinal axis, a proximal end for being disposed externally and a distal end for being disposed in the body and an open lumen extending from said proximal end through said distal end, said elongate hollow being adapted to be inserted through a portal into the body;
   b) an endoscope comprising
      b1) an elongate member having a longitudinal axis, a proximal end and a distal end, said elongate member extending through at least a portion of said hollow barrel lumen, b2) a substantially planar complementary metal oxide semiconductor (CMOS) chip including an image sensor having a plurality of pixels and a pixel signal processing circuit generating an image ready signal, converting image light energy into electrical image ready signal energy, for transmission out of the body, said image ready signal adapted to be viewed on an image display; said CMOS image sensor being carried on said elongate member, adjacent said distal end;

b3) an objective lens carried on said elongate member distal end on an optical axis and focusing an image corresponding to an endoscope field of view at an image plane intersecting said optical axis; said CMOS image sensor pixels being disposed in said image plane and on said optical axis.

b4) said chip further including a physical parameter sensor;

c) said elongate member being slidably carried in said barrel; and d) a repositionable mount carrying said image display and comprising a flexible stalk supporting an image display panel.

7. The instrument of claim 6, said physical parameter sensor comprising a CMOS thermistor temperature sensor.

8. The instrument of claim 6, further including at least one fixed focus objective lens element having a depth of field with a selected minimum in-focus distance for an in-focus image at the image plane.

9. The endoscope of claim 8, further including a color mosaic optical filter disposed between said CMOS image sensor and said objective lens, said color mosaic optical filter being disposed on said optical axis.

10. The instrument of claim 8, further comprising a surgical instrument end effector carried by said elongate hollow barrel, said end effector having a selected length being substantially equal to or greater than said endoscope minimum in-focus distance.

11. A surgical endoscopic instrument for viewing and manipulating anatomical tissue or other object in a body, comprising:

a) an elongate member having a longitudinal axis, a proximal end for being disposed externally and a distal end for being disposed in the body, said elongate member adapted to be inserted through a portal into the body and having an end effector of a selected length carried on said elongate member distal end;

b) a substantially planar complementary metal oxide semiconductor (CMOS) chip including an image sensor having a plurality of pixels and a pixel signal processing circuit generating an image ready signal, converting image light energy into electrical image ready signal energy, for transmission out of the body, said image ready signal adapted to be viewed on an image display; said CMOS image sensor being carried on said elongate member, adjacent said distal end, said chip further including a physical parameter sensor;

c) an objective lens carried on said elongate member distal end on an optical axis and focusing an image corresponding to an endoscope field of view at an image plane intersecting said optical axis; said CMOS image sensor pixels being disposed in said image plane and on said optical axis;

d) a light source carried by said elongate member and illuminating the endoscope field of view; and e) a repositionable mount carrying said image display and comprising a flexible stalk supporting an image display panel.

12. The endoscope of claim 11, further including a color mosaic optical filter disposed between said CMOS image sensor and said objective lens, said color mosaic optical filter being disposed on said optical axis.

13. The instrument of claim 11, further including at least one fixed focus objective lens element having a depth of field with a selected minimum in-focus distance for an in-focus image at the image plane, said minimum in-focus distance being less than or substantially equal to said end effector selected length.

14. The instrument of claim 13, wherein said end effector is a forceps instrument for viewing and manipulating anatomical tissue or other objects, in the body, comprising first and second opposable forceps jaws hingedly mounted on said elongate member distal end; said jaws having said selected end effector length.

15. The instrument of claim 14, further including a housing carrying said elongate member proximal end, said housing carrying at least one handle, at least one of said jaws being responsive to said handle.

16. An endoscopic forceps instrument for viewing and manipulating anatomical tissue, organs or other objects, in the body, comprising:

a) a housing having an exterior wall enclosing an interior volume;

b) at least one articulable handle carried on said housing; said handle adapted to be grasped and manipulated by hand;

c) an elongate hollow barrel having a longitudinal axis, a proximal end for carried by said housing externally, a distal end for being disposed in the body and an open lumen extending from said proximal end through said distal end, said elongate hollow barrel being adapted to be inserted through a portal into the body;

d) first and second opposable forceps jaws hingedly mounted on said elongate hollow barrel distal end; at least one of said forceps jaws being responsive to said handle, said jaws having a selected length;

e) an endoscope comprising e1) an elongate member having a longitudinal axis, a proximal end and a distal end, said elongate member extending through at least a portion of said hollow barrel lumen, e2) a substantially planar complementary metal oxide semiconductor (CMOS) chip having an image sensor including a plurality of pixels and a pixel signal processing circuit generating an image ready signal, converting image light energy into electrical image ready signal energy, for transmission out of the body, said image ready signal adapted to be viewed on an image display; said CMOS image sensor being carried on said elongate member, adjacent said distal end;

e3) an objective lens carried on said elongate member distal end on an optical axis and focusing an image corresponding to an endoscope field of view at an image plane, intersecting said optical axis; said CMOS image sensor pixels being disposed in said image plane and on said optical axis;

e4) said chip further including a physical parameter sensor;

f) said elongate member being slidably and rotatably carried in said barrel; and g) a repositionable mount carrying said image display and comprising a flexible stalk supporting an image display panel.

17. The endoscopic forceps instrument of claim 16, said physical parameter sensor comprising a CMOS thermistor temperature sensor.

18. The instrument of claim 16, further including at least one fixed focus objective lens element having a depth of field with a selected minimum in-focus distance for an in-focus image at the image plane, said minimum in-focus distance being less than or substantially equal to said forceps jaw selected length.

19. A surgical endoscopic instrument for viewing anatomical tissue or other object in a body, comprising:
   a) an elongated hollow barrel having a distal end and a proximal end;
   b) an endoscope comprising
      b1) an elongate body having a longitudinal axis, a proximal end and a distal end, said elongate body extending through at least a portion of said barrel,
      b2) a CMOS image sensor and a CMOS physical parameter sensor carried by said elongate body;
   c) said elongate body being movably carried in said barrel; and
   d) a repositionable mount carrying an image display and comprising a flexible stalk supporting an image display panel.

20. The instrument of claim 19, wherein rigid elongate body is carried in said barrel to rotate about said elongate body longitudinal axis.

21. The instrument of claim 19, further including a light source carried by said elongate body.

22. The instrument of claim 19, wherein said CMOS image sensor and said CMOS physical parameter sensor are carried on said elongate body distal end.

23. An endoscope, comprising:
   a) an elongate body having a longitudinal axis, a proximal end and a distal end;
   b) a CMOS image sensor substrate carried on said elongate body;
   c) a physical parameter sensor fabricated onto said substrate; and
   d) a repositionable mount carrying said image display and comprising a flexible stalk supporting an image display panel.

24. The endoscope of claim 23, wherein said physical parameter sensor is a temperature sensor.

* * * * *